United States Patent [19]

Gammill et al.

[11] Patent Number: 5,180,717
[45] Date of Patent: Jan. 19, 1993

[54] BIVALENT LIGANDS EFFECTIVE FOR BLOCKING ACAT ENZYME FOR LOWERING PLASMA TRIGLYCERIDES AND FOR ELEVATING HDL CHOLESTEROL

[75] Inventors: Ronald B. Gammill, Portage; Frank P. Bell, Vicksburg, both of Mich.

[73] Assignee: The Upjohn Company, Kalamazoo, Mich.

[21] Appl. No.: 697,301

[22] Filed: May 7, 1991

Related U.S. Application Data

[63] Continuation-in-part of Ser. No. 486,648, Feb. 28, 1990, abandoned, and a continuation-in-part of Ser. No. 651,334, Feb. 8, 1991, abandoned, which is a continuation-in-part of Ser. No. 2,572, Jun. 16, 1989, which is a continuation of Ser. No. 232,931, Aug. 16, 1988, abandoned.

[51] Int. Cl.$^5$ .......................................... A61K 31/445
[52] U.S. Cl. .................................. 514/63; 514/224.5; 514/232.2; 514/253; 514/316; 514/455; 544/55; 544/78; 544/82; 544/229; 544/316; 544/357; 544/375; 544/378; 546/14; 546/186; 546/187; 548/406; 548/518; 549/214; 549/387
[58] Field of Search .................. 514/63, 229.8, 224.5, 514/231.5, 231.8, 252, 253; 546/187; 544/95, 378, 357, 375

[56] References Cited

U.S. PATENT DOCUMENTS

| | | | |
|---|---|---|---|
| 3,816,467 | 6/1974 | Wright | 544/378 |
| 4,281,013 | 7/1981 | Schurr | 514/455 |
| 4,284,569 | 8/1981 | Gammill | 544/378 |
| 4,304,722 | 12/1981 | Gammill | 544/378 |
| 4,412,071 | 10/1983 | Gammill | 544/58.6 |
| 4,434,295 | 2/1984 | Gammill | 546/187 |
| 4,540,798 | 9/1985 | Gammill | 549/387 |
| 4,593,027 | 6/1986 | Winklemann | 514/253 |
| 4,820,851 | 4/1989 | Gammill | 549/462 |

FOREIGN PATENT DOCUMENTS

90/02129 3/1990 PCT Int'l Appl. .................. 546/187

OTHER PUBLICATIONS

Bell, F. P., "Arterial Cholesterol Esterification by AcylCoAcholesterol Acyltransferase: Its Possible Significance in Atherogenesis and its Inhibition by Drugs," Pharmacological Control of Hyperlipidaemia, J. R. Prous Science Publishers, S. A., pp. 409-422 (1986).

DeVries, V. G., et al., "Potential Antiatherosclerotic Agents. 5. An Acyl-CoA:Cholesterol O-Acyltransferase Inhibitor with Hypocholesterolemic Activity," Journal of Medicinal Chemistry, 29, 7, pp. 1131-1133 (1986).

DeVries, V. G., et al., "Potential Antiatherosclerotic Agents. 4. [(Functionalized-alkyl)amino]benzoic Acid Analogues of Cetaben," Journal of Medicinal Chemistry, 26, 10, pp. 1411-1421 (1983).

Suckling, K. E., et al., "Role of acyl-CoA:cholesterol acyltransferase in cellular cholesterol metabolism," Journal of Lipid Research, 26, pp. 647-671 (1985).

Erden et al CA, 17449n (1984) vol. 100.

Gammill et al. Jour. Med Chem. vol. 33, pp. 2685-2687 (1990).

Primary Examiner—Donald G. Daus
Attorney, Agent, or Firm—Thomas A. Wootton; Donald L. Corneglio

[57] ABSTRACT

Bivalent ligand compounds synthesized from a tether composition joining two heterocyclic groups comprising furochromones, furobenzoxazinones, and benzobisdifurans. These compounds show pharmacological activity in blocking ACAT enzymes which are major regulators of cholesterol metabolism. The compounds also show activity in lowering plasma triglycerides and elevating HDL cholesterol. They are useful in the prevention or treatment of the constriction or obstruction of arterial vessels, atherosclerosis, hyperlipidemia, hypertriglyceridemia, chylomicronemia, and pancreatitis.

16 Claims, No Drawings

BIVALENT LIGANDS EFFECTIVE FOR BLOCKING ACAT ENZYME FOR LOWERING PLASMA TRIGLYCERIDES AND FOR ELEVATING HDL CHOLESTEROL

CROSS-REFERENCE TO RELATED PATENT APPLICATIONS

This application is a continuation-in-part of two U.S. patent applications, U.S. Ser. No. 07/486,648 filed Feb. 28, 1990 and U.S. Ser. No. 07/651,334 filed Feb. 8, 1991, both now abandoned which were continuation-in-part applications of PCT/US89/02572 pending filed in the U.S. Receiving Office Jun. 16, 1989, which was a continuation of U.S. Ser. No. 07/232,931 filed Aug. 16, 1988, abandoned.

BACKGROUND OF THE INVENTION

The present invention is directed toward bivalent ligands effective for blocking or inhibiting acyl-CoA; cholesterol O-acyltransferase enzyme (hereinafter, ACAT) which is a major regulator of cholesterol metabolism in cells. The blocking or inhibition of ACAT is useful in the prevention or treatment of a variety of physiological conditions associated with arterial vessels. In addition to the inhibition of ACAT the compounds have also been discovered to be effective in the lowering of plasma triglyceride levels and as a high-density lipoprotein (HDL) cholesterol elevator.

ACAT is found in most tissues including arterial, liver, adrenal gland, mammary gland, ovaries and intestine where it readily converts cholesterol into esterified cholesterol. Bell, F. P., Arterial Cholesterol Esterification By AcylCoAcholesterol Acyltransferase: Significance in Atherogenesis and its Inhibition by Drugs, Pharmacological Control of Hyperlipidaemia, JR Prous Sci. Pub., pp 409-422 (1986). Generally this reaction is in equilibrium with a hydrolysis reaction which converts the esterified cholesterol into cholesterol. The amount of available cholesterol which effects the balance of this equilibrium is dependent on many physiological factors and diet. Unfornutately, esterified cholesterol does not migrate through tissue as easily as cholesterol and can build-up and form obstructions. The accumulation of esterified cholesterol is one of the characteristic features of atheroschlerotic plaque. Therefore it would be of great advantage if the ACAT enzyme could be blocked or inhibited from turning cholesterol into esterified cholesterol in arterial tissues. Thus the compounds would be particularly useful in the treatment of the constriction or obstruction of arteries and atheroschlerosis.

These compounds, which are useful as ACAT inhibitors, also have the unprecedented effect of lowering plasma triglycerids and elevating HDL cholesterol. The potent hypotriglyceride effect of these compounds indicates that they would be useful in treating a variety of disorders associated with elevated triglyceride such as hyperlipidemia, hyperlipoproteinemia, hypertriglyceridemia, hypercholesterolemia, chylomicronemia, and related disorders such as pancreatitis.

Triglyceride lowering is recognized as a desirable therapeutic goal given that elevated triglyceride levels are positively associated with pancreatitis and coronary artery disease in humans and are commonly seen in Type IV and Type V hyperlipoproteinemic patients and are associated with obesity, diabetes, $\beta$-blocker therapy and chronic renal failure. The elevation of HDL cholesterol is also recognized as a desirable therapeutic goal in treating and preventing coronary artery diseases.

INFORMATION DISCLOSURE

The literature discusses the use of ACAT inhibitors as potential antiatherosclerotic agents as disclosed in V. G. DeVries, et al., J. Med. Chem., 29, 1131 (1986) and J. Med. Chem., 26, 1411 (1983). Also, the role of acyl-CoA:cholesterolacyltransferase in cellular cholesterol metabolism is discussed in K. E. Suckling and E. F. Stange, J. Lipid Res., 26, 647 (1985).

The subject bivalent ligands are represented by $\alpha$-$\beta$-$\alpha$ where $\beta$ is a chemical tether connecting two heterocyclic groups $\alpha$. The heterocyclic groups are furochromones, furobenzoxazines and benzodifurans which are generally disclosed in U.S. Pat. Nos. 4,284,569, 4,412,071 and 4,304,722.

SUMMARY OF THE INVENTION

The present invention is directed to a family of bivalent ligands useful as ACAT inhibitors in addition to lowering plasma triglyceride levels and elevating HDL cholesterol levels in patients, such as mammals, by administering a therapeutically effective amount of a compound or its pharmaceutical salt. The family of bivalent ligands, $\alpha$-$\beta$-$\alpha$, are formed from two heterocyclic compounds "$\alpha$" connected by a tether "$\beta$", wherein "$\alpha$" is structurally represented by the formula below

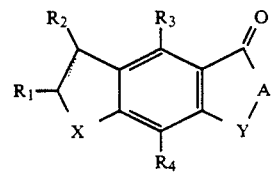

wherein

X and Y are independently O, N or S;

A is C=CH—$\beta$, N=C—$\beta$ or CR$_5$=C—(CH$_2$)$_n$—$\beta$;

R$_1$ and R$_2$ are independently: H, halo, alkyl, —(CH$_2$)$_p$-aryl, —(CH$_2$)$_p$-heteroaryl, —(CH$_2$)$_p$—CO$_2$R$_6$, —(CH$_2$)$_p$—CONR$_7$R$_8$, —Si(R$_9$), —(CH$_2$)$_n$-NR$_7$R$_8$, —(CH$_2$)$_n$—OR$_{10}$, —CF$_3$, or —(CH$_2$)$_n$—SR$_6$, —(CH$_2$)$_n$—SOR$_6$, —(CH$_2$)$_n$—SO$_2$R$_6$;

R$_3$ is OH, OCH$_2$CH=CH$_2$, OCH$_2$C-H(OH)CH$_2$NHR$_6$, —O-alkyl, —O-alkyl, —O—(CH$_2$)$_n$—CO$_2$R$_6$, or —O—(CH$_2$)$_n$—CONR$_7$R$_8$;

R$_4$ is hydrogen, halo, NO$_2$, NH$_2$, CF$_3$, alkyl, aryl, —S-alkyl or aryl, —SO$_2$-alkyl or aryl, R$_3$, or —(CH$_2$)$_n$—NR$_7$R$_8$;

R$_5$ is a hydrogen, NO$_2$, NH$_2$, CF$_3$, alkyl, aryl, —S-alkyl, —S-aryl or heteroaryl, —SO-alkyl or aryl, —SO$_2$-alkyl or aryl, or R$_3$;

R$_6$ is H, CF$_3$, alkyl or aryl, Li$^+$, Na$^+$, K$^+$, Ca$^{2+}$ and other pharmaceutically acceptable counter ions for carboxylic acids;

R$_7$ and R$_8$ are H, CO-alkyl, CO-aryl, alkyl, cycloalkyl, alkylaryl, heteroalkyl, aryl, or R$_7$ and R$_8$ can be taken together to form a piperidine ring or morpholine ring;

R$_9$ is an alkyl or aryl;

R$_{10}$ is H, CF$_3$, alkyl, aryl or heteroaryl; and n is 0-5 and p is 0-8; and $\beta$ is selected from the group A-E consisting of:

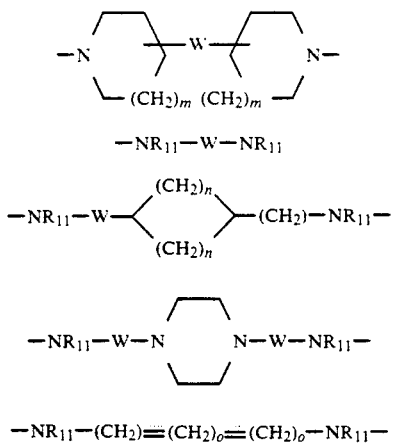

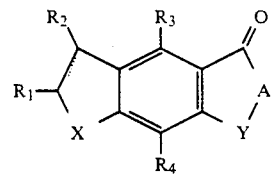

wherein:
W is —CH$_2$—(X$_n$—CH$_2$)$_n$;
X is N, O or S;
R$_{11}$ is an alkyl, CO-alkyl or CON-alkyl or -aryl; and
m is 0–4, n is 0–5 and o is 1–5.

The preferred tethers are trimethylene-4,4-dipiperidine, 1,2-ethanediyl-4,4-dipiperidine, 1,4-bis(aminopropylpiperazine), or 1,8-diaminooctane. One example of a bivalent ligand composition is 7,7′-(1,2-ethanediylbis(4,1-piperidinediylmethylene))-bis(4,9-dimethyl-5H-furo (3,2-g)(1)-benzopyran-5-one.

In one aspect, the subject bivalent ligands provide a method for blocking or inhibiting ACAT enzyme by administering a pharmacological amount of the composition or an acceptable salt thereof to a subject including humans. The blocking or inhibition of ACAT is useful in the prevention or treatment of a variety of physiological conditions associated with arterial vessels. The use is particularly suitable for administration subsequent to by-pass surgery, coronary by-pass surgery, angioplasty or transplants.

In another aspect, the subject bivalent ligands provide a use for preventing or treating hyperlipidemia, hyperlipoproteinemia, hypertriglyceridemia, chylomicronemia and related disorders such as pancreatitis or atheroschlerosis by administering a pharmacological amount of the composition or an acceptable salt thereof to a subject, including humans.

In another aspect, the subject compounds provide a method for lowering plasma triglycerides and elevating HDL cholesterol. This therapeutic affect is useful in the treatment of hyperlipidemia, hyperlipoproteinemia, hypertriglyceridemia, hypercholesterolemia, chylomicronemia, pancreatitis and related arterial and heart disorders.

DETAILED DESCRIPTION OF THE INVENTION

The compounds of the present invention are bivalent ligands, represented by "α-β-α", such as bisaminofurochromone and bisaminobenzodifurans formed from two heterocyclic ring structures "α" linked by a chemical tether "β" of varying composition. The heterocyclic structure "β", furochromones, furobenzoxazines and benzodifurans, are disclosed in U.S. Pat. Nos. 4,284,569, 4,412,071 and 4,304,722 where they are reported to be antiatherogenic compounds having antiatheroschlerosis activity. Their synthesis are disclosed in U.S. Pat. Nos. 4,284,569, 4,412,071 and 4,304,722 which are herein incorporated by reference. The heterocyclic compounds can be generically depicted by the structural formula "α" as shown below; wherein X and Y are independently O, N or S;
A is C═CH—β, N═C—β or CR$_5$═C—(CH$_2$)$_n$—β;
R$_1$ and R$_2$ are independently: H, halo, alkyl, —(CH$_2$)$_p$-aryl, —(CH$_2$)$_p$-heteroaryl, —(CH$_2$)$_p$—CO$_2$R$_6$, —(CH$_2$)$_p$—CONR$_7$R$_8$, —Si(R$_9$), —(CH$_2$)$_n$—NR$_7$R$_8$, —(CH$_2$)$_n$—OR$_{10}$, —CF$_3$, or —(CH$_2$)$_n$—SR$_6$, —(CH$_2$)$_n$—SOR$_6$, —(CH$_2$)$_n$—SO$_2$R$_6$;
R$_3$ is OH, OCH$_2$CH═CH$_2$, OCH$_2$CH(OH)CH$_2$NHR$_6$, —O—alkyl, —O—(CH$_2$)$_n$—CO$_2$R$_6$, or —O—(CH$_2$)$_n$—CONR$_7$R$_8$;
R$_4$ is hydrogen, halo, NO$_2$, NH$_2$, CF$_3$, alkyl, aryl, —S-alkyl or aryl, —SO-alkyl or aryl, —SO$_2$-alkyl or aryl, R$_3$, or —(CH$_2$)$_n$—NR$_7$R$_8$;
R$_5$ is a hydrogen, NO$_2$, NH$_2$, CF$_3$, alkyl, aryl, —S-alkyl, —S-aryl or heteroaryl, —SO-alkyl or aryl, —SO$_2$-alkyl or aryl, or R$_3$;
R$_6$ is H, CF$_3$, alkyl or aryl, Li$^+$, Na$^+$, K$^+$, Ca$^{2+}$ and other pharmaceutically acceptable counter ions for carboxylic acids;
R$_7$ and R$_8$ are H, CO-alkyl, CO-aryl, alkyl, cycloalkyl, alkylaryl, heteroalkyl, aryl, or R$_7$ and R$_8$ can be taken together to form a piperidine ring or morpholine ring;
R$_9$ is an alkyl or aryl;
R$_{10}$ is H, CF$_3$, alkyl aryl or heteroaryl; and
n is 0–5 and p is 0–8.

The tether or connector "β" for two of the heterocyclic groups selected from those compounds disclosed above, is chosen from one of the tether "β" structural formulae (A-E), consisting of:

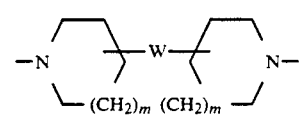

A)

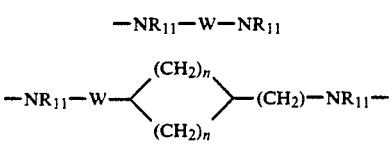

B)

C)

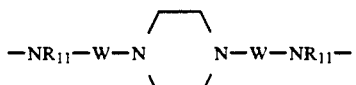

D)

E)

wherein
W is —CH$_2$—(X$_n$—CH$_2$)$_n$;
X is N, O or S;
R$_{11}$ is an alkyl, CO-alkyl or CON-alkyl or -aryl; and
m is 0–4, n is 0–5 and o is 1–5.

"Alkyl" is defined as one to 8 carbon atoms and their isomeric forms. The definition includes but is not limited to methyl, ethyl, propyl, butyl, pentyl, hexyl, heptyl, octyl and isomeric forms thereof.

"Aryl" is defined as 6 to 12 carbon atoms. The definition includes but is not limited to α-naphthyl, β-naphthyl, m-methylphenyl, p-trifluoromethylphenyl and the like. The aryl groups can also be substituted with one to 3 hydroxy, $C_1$-$C_3$ alkoxy, $C_1$-$C_3$ alkyl, trifluorometnyl, fluoro, chloro, or bromo groups.

"Cycloalkyl" is defined as 3 to 10 saturated cyclic. The definition includes but is not limited to cyclopropyl, cyclobutyl, cyclopentyl, cyclohexyl, cycloheptyl and cyclodecyl.

"Alkylaryl" is defined as alkyl chains of one to 8 carbon atoms and isomeric forms thereof which are substituted with aryl groups of 6 to 12 carbon atoms as described above.

"Heteroaryl" is defined as 6 to 12 carbon atom aryls as described above containing heteroatoms selected from nitrogen, sulfur and oxygen. Examples can include pyridine, thiophene, furan and pyrimidine.

"Heteroalkyl" is defined as two to 8 carbon atoms alkyls as described above which contain heteroatoms selected from nitrogen, sulfur and oxygen.

"Halo" is defined as the halogens which include fluorine, chlorine, bromine and iodide.

Connecting two of the heterocyclic groups "α" with one of the tethers "β" produces a compound that inhibits ACAT, lowers plasma triglycerides and raises HDL cholesterol. The heterocyclic groups are bound to the tether directly by the nitrogen atoms present at each end of the tether or through from one to about 5 carbon atoms to the nitrogen atom present at the end of the tether. Generally the heterocyclic group is the same at both ends of the tether however the bivalent ligands can comprise a different heterocyclic group at either end of the tether. Regardless, tethering two heterocyclic structures together provides greater potency and those tethers containing heteroatoms appear to improve the interaction of the bivalent ligand with the tissue for inhibiting ACAT, lowering plasma triglycerides and elevating HDL cholesterol levels.

Various chemical schemes for preparing these compounds are described below. The specific structures for compounds prepared according to this invention as shown in Tables 1-4 along with their measured inhibition of ACAT at various levels.

The ratio of $^3$H-cholesteryl ester radioactivity to the sum of the $^3$H-cholesterol plus $^3$H-cholesteryl ester recovered in the cellular extracts X 100 yields the percent of total $^3$H-cholesterol taken up which was esterified by cellular ACAT and is referred to as percent ACAT. Percent inhibition of ACAT is also mathematically derived from the data for convenience. Values for % ACAT that are less than control values identify assay cultures in which ACAT was inhibited; the positive standard values provide a basis for relative potency evaluation. Control values for percent ACAT typically range from 60-70% under the rest conditions employed.

Compound I (Table 1) is prepared by the treatment of C-7 methylthiomethylsulfide with excess methyl iodide in methylene chloride at reflux for 72 hours to produce the allylic iodide form in a 70 to 75% yield as a pale yellow solid. This product is then treated with trimethylene-4,4-piperidine in acetonitrile in the presence of potassium carbonate to yield the allylic bisamine form, i.e., Compound I, as a powdery solid.

The synthesis of the bisaminofurobenzoxazinone, Compound II (Table 1) is performed by oxidation of khellin with basic hydrogen peroxide followed by esterification of the resulting acid which affords the hydroxyester. See, U.S. Pat No. 4,412,071. Treatment of the hydroxy ester with cyanogen bromide in the presence of triethylamino (TEA) in acetonitrile yields the cyanoether. The cyanoether is then treated with trimethylene-4,4-piperidine ion acetonitrile, to yield the bisaminofurobenzoxazinone, i.e., Compound II.

The synthesis of the benzodifurans, Compounds III (Table 1) (see, Example 1, below) is accomplished by addition of diamines to bromofurochromone or bromochromone, respectively. The addition is performed in the presence of potassium carbonate and acetonitrile.

Compounds I-III are prepared with the trimethyl-4,4-dipiperidine tether and their structure and percent ACAT inhibition in micrograms per milliliter (μg/ml) is shown in Table 1. Included in Table 1 is the single heterocyclic compound IV of Compound I which shows reduced percent ACAT inhibition and demonstrates the enhanced potency observed in the corresponding bivalent ligand Compound I.

The effect of varying the tether where the heterocyclic compound is the furochromone, Compound I, is shown in Table 2 as Compound I(a-d). Compound I is the compound from Table 1. The tether structure is shown with the percent ACAT inhibition for the bivalent compound. Table 3 shows the results of varying the groups on the bisaminofurochromone of Compound Ia.

The synthesis of the dihydrofurochromone containing Compound V (Table 3) begins with khellinone, a basic hydrolysis product of khellin. Hydrogenation of khellinone proceeds quantatively to give a product which is then subject to claisen condensation with ethyl (α-thiomethyl) acetate followed by acid catalyzed cyclodehydration to yield dihydrofurochromone. Treatment of the dihydrofurochromone with methyl iodide and methylene chloride at reflux affords the desired allylic iodide. Treatment of the allylic iodide with dimethylene-4,4-piperidine yields the dihydro analog, Compound V.

The trimethylsilyl analog, Compound VI (Table 3) (see Example 6, below) is prepared in the following manner. Treatment of timefurone with two equivalents of lithium diisopropylamide (LDA) results in the formation of a dilithio species which when treated with trimethylsilyl chloride and subjected to an aqueous workup affords the 2-trimethylsilyl analog in good yield. Treatment of this product with excess methyl iodide in methylene chloride affords the allylic iodide. Addition of dimethylene-4,4-piperidine to the allylic iodide yields the desired bisaminofurochromone, Compound VI in 75.5% yield.

Table 4 shows bisaminobenzodifuran compounds with various substitutions and their bisaminofuran counterparts. A comparison of the percent inhibition of ACAT shows that Compound IX exhibits excellent inhibition over its monomeric counterparts. While Compound VII is active at the high dose tested (15 μg/ml), Compound IX shows surprisingly good inhibitory activity even at the 5 μg/ml dose. The data indicates that the bivalent bisaminobenzodifurans are more potent at a lower dose which shows an advantage over their monomeric counterparts (compare the 5 μg/ml dose Compound IX with the difuran analogs, see Table 4).

The present invention has identified classes of compounds which are structurally unique, inhibit ACAT, lower plasma triglycerides, and elevate HDL cholesterol. The data indicates the preferred compounds are those such as Compound Ia (Table 2), bisaminofurochromone, the preparation of which is described in Example 2 below.

These compounds have been shown to also exhibit antiatherosclerotic activity in the SEA Japanese quail model and Netherland Dwarf rabbit. For example, five to six week old, male, SEA quails were placed on a high chloesterol diet with one group orally receiving the subject ACAT inhibitor compound Ia (Table 2). After eight weeks the arteries were removed, cleaned and homogenized. Total chloesterol, free cholesterol and triglycerides were measured. The results were statistically analyzed and showed a significant (thirty percent) reduction in the accumulation of esterified chloesterol in the arteries for quails that received the ACAT inhibitor compound.

In another experiment, ACAT inhibitor compound Ia (Table 2) was administered for twelve weeks at 50 mg/kg/day to Netherland dwarf rabbits that were feed a chloesterol-containing atherogenic diet. During the twelve week period serum cholesterol, triglycerides, and carnitine were monitored. At the end of the study the aortas from the drug treated group and a non-drug treated group were examined for atheroschlerosis development.

There was less extensive development of hypercholesterolemia in the treated group. The mean serum cholesterol levels in the control exceeded 2200 mg/dl whereas the mean levels in the treated group was 271 mg/dl. The lower serum cholesterol level was associated with negligible atheromatous lesion development in the treated groups. In contrast, atheromatous lesion development in the controls was extensive.

It has been concluded that the compounds of the present invention are pharmacologically effective in the reduction of esterified cholesterol not only in the general prevention or treatment of cholesterol levels but also in other physiological conditions associated with the occlusion or obstruction of arteries. For example, the subject bivalent ligands can be useful in preventing arterial occlusion in vascular trauma associated with procedures such as by-pass grafts, coronary by-passes, angioplasty and transplants.

In addition to the measured inhibition of ACAT described above, Compound Ia (Table 2) was administered to genetically obese Zucker rats as described below and is shown to have potent hypotriglyceridemic action. The experiments conducted showed a dose-dependent reduction in plasma triglycerides and a dose dependent elevation of plasma HDL cholesterol without significant changes in plasma total cholesterol. The Zucker rat assay is art recognized for its ability to predict the ability of a compound to lower triglycerides or increase HDL-cholesterol such as reported in Zucker, L. M., "Hereditary obesity in the hyperlipemia," Ann. NY Acad. Sci., 131, 447 (1965); Barry, W. S., & Bray, G. A., "Plasma triglycerides in genetically obese rats," Metabolism, 18, 833 (1969); Schofeld, G., et al., "Characterization of the plasma lipoproteins of the genetically obese hyperlipoproteinemic Zucker fatty rat," J. Lipid Res., 15, 457 (1974); and Simonelli, C., and Eaton, R. P., "Effect of clofibrate on in vivo triglyceride production and clearance in genetically hyperlipemic rates," Atheroschlerosis, 29, 269–275 (1978). Two studies follow:

Hypertriglyceridemia Model

Female Zucker rats (fafa, 378±3) were maintained on a pelleted chow diet (Purina Chow #5001) or the chow diet which contained compound Ia (Ia) at a level calculated to deliver 50 mg/kg/day. The Ia containing pellets were prepared from #5001 meal into which the drug had been pre-mixed and subsequently pelletized. Plasma cholesterol and triglyceride levels were measured at weekly intervals over a 21-day period after which time both groups of rats were crossed-over. The plasma was obtained from heparinized blood taken by cardiac puncture and the lipids were measured using an Ektachem DT60 analyzed (Eastman Kodak).

Within 8 days after the addition of Ia to the diet, plasma triglycerides were reduced significantly from a group mean of 2431±446 to 260±52 mg/dl. The reduction in triglycerides was evident in each of the five treated rates. Triglyceride levels continued to stay at the reduced level as long as the drug was administered. On day 16, drug was withdrawn and triglyceride levels essentially returned to pretreatment levels within 1 week without evidence of any uniform tendency to overshoot. The control group, which was run in parallel with the treatment group, maintained plasma triglycerides within the expected range until cross-over to Ia on day 27. As was observed with the initial treatment group, the controls displayed a remarkable reduction in plasma triglycerides during the 5 day cross-over period; triglycerides were reduced from 2872±742 to 656±242 mg/dl.

Plasma cholesterol levels were also monitored during these experiments. Mean plasma cholesterol levels rose from 126±18 to 174±8 mg/dl with Ia administration and all but one responded with a cholesterol elevation. Upon withdrawal of the drug (day 16), plasma cholesterol levels were restored essentially to pretreatment levels. The control group maintained plasma cholesterol levels within a tight range until being cross-over to Ia at day 27; after cross-over, plasma cholesterol rose from 118±24 to 164±22 mg/dl with three out of four animals showing the increase.

In this rat model, which is considered to be a model of Type IV hyperlipoproteinemia in man (Schonfeld, G. et al., "Characterization of the Plasma Lipoproteins of the Genetically Obese Hyperlipoproteinemic Zucker Obese Rats, J. Lipid R., 15, 457–464 (1974), Ia induced a remarkable reduction in the plasma triglycerides from levels as high as 3000 mg/dl to less than 300 mg/dl. Of added interest is the observation that the subject compound has very little effect on plasma triglyceride levels in rats or rabbits whose triglycerides are within normal limits.

Hypercholesterolemic Model

Obese female Zucker rats (fa/fa) weighing 500–600 g were used in the study. These animals are endogenously hypertriglyceridemic and hypercholesterolemic as was described above. Basal plasma triglycerides, cholesterol, and HDL-C levels were determined in individual rats (Ektachem DT 60 Analyzer) which were then randomly assigned to four Compound IA (Ia) treatment groups (5 mg/kg, n=4; 10 mg/kg, n=4; 20 mg/kg, n=4; 30 mg/kg, n=3). The animals were all individually housed and received Purina Chow pellets (#5002)

containing IA at levels calculated to provide the daily doses of Ia described above. After 1 week, all rats were bled by cardiac puncture for determination of plasma triglycerides, cholesterol, and HDL-C. An additional group of rate (n=3), receiving chow alone was run in parallel with the treatment groups as an additional control for the experiment. Each animal acted as its own control since plasma lipid parameters were measured in each animal immediately prior to dosing. The data for triglycerides, cholesterol, and HDL-C were adjusted for this pre-dosing value using a percent change calculation: (Post-Pre)/Pre)100. For all 3 measurements, a simple linear model was fit to the percent change value vs log 10 (dose). The logarithmic transformation was used to linearalize the relationship.

The results demonstrated a significant negative relationship between % change in plasma triglycerides and log 10 (dose). The predicted linear equation was % change triglyceride=41.3−73.6 log 10 dose. The negative slope was significantly different from zero ($P<0.008$). In contrast, the results showed a significant linear positive relationship between the % change HDL-C and log (10 (dose). The estimated linear equation was % change HDL-C=046.9+68.7 log 10 dose. The positive slope was statistically significant from zero ($P<0.04$).

In the group of rats which continued to receive chow diet alone throughout the experiment period, their lipid parameters remained constant (baseline values vs 1 week values for triglyceride, cholesterol, and HDL-C were, respectively, 173±48 vs 166±35; 1506±546 vs 1325±551; 86±17 vs81±19).

In conclusion, the results of this study confirmed the triglyceride lowering activity of Ia and indicated that the effects are linearly related to dose. Additionally, the data indicated that the hypotriglyceridemic effect can be dissociated from a tendency to elevate plasma cholesterol in this model. The other noteworthy effect was that the subject compound had the ability to elevate HDL-cholesterol. The well established negative correlation between HDL-C and heart attack risk, the positive correlation between plasma triglyceride and heart atack risk and the putative benefit of ACAT inhibition would indicate that Ia is a singular compound with the potential for efficacy in treating disorders of lipid metabolism and their consequences (i.e. atherosclerotic vessel disease).

Evidence that patients can be helped by lowering triglycerides and raising high density lipids (HDL) is reported in Fontbonne A., Eschwege, E. et al. "Hypertriglyceridaemia as a risk factor of coronary heart disease mortality in subjects with impaired glucose tolerance or diabetes. Results from the 11-year follow-up of the Paris Prospective Study." Diabetologia, 32, 300–304 (1989); Carlson, L. A. & Bottiger, L. E., "Risk factors for Ischaemic heart disease in men and women. Results of the 19-year follow-up of the Stockholm Prospective Study," Acta Med Scand, 218, 207–211 (1985); and Castelli, W. P., "The triglyceride issue: A view from Framingham," Am. Heart J., 112, 432–437 (1986).

Further, in men and women elevation of HDL levels of possession of high HDL levels is stated in the medical literature to be associated with decrease risk for myocardial infarctions, such as Rifkind, B. M., "High-density lipoprotein cholesterol and coronary artery disease: Survey of the evidence," Am J Cardiol., 66, 3A–6A (1990); Wilson, P. W. F., "High-density lipoprotein, low density lipoprotein and coronary artery disease," Am J Cardiol., 66, 7A–10A (1990); Brown, W. V., "Clinical trials including an update on the Helsinki Heart Study," Am J Cardiol., 66, 11A–15A (1990),; and Brunner, D., Bearman, J., Waysbort, J., Schwartz, S. and Loebl, K., "High density lipoprotein cholesterol percentage and incidence and mortality of myocardial infarction: 20 year follow-up of the Donolo-Tel Aviv Coronary Artery disease study." In: Pharmacological Control of Hyperlipidaemia, Ed by R. Fears, R. I. Levy, J. Shepherd, C. J. Packard and N. E. Miller. J. R. Prous Science Publishers, Barcelona, pp 509–510 (1986).

the dose of the bivalent ligand compound used in treatment depends on the particular use, frequency of administration and the age or condition of the recipient. Thus, the subject compounds along with any carriers or buffers would be administrated in a therapeutic or pharmacological amount effective to inhibit ACAT enzyme as prescribed, lower plasma triglycerides or elevate HDL cholesterol with respect to the physiological condition diagnosed such as atheroschlerosis, high blood cholesterol, artery occlusion or restriction, or surgical procedure as well as factors such as diet. Generally, the compounds can be administered in an amount of from about 0.1 to about 1000.0 mg/kg per dose.

The compounds can be administered intravenously, intramuscularly, topically, transdermally such as by skin patches, bucally or orally to man or other animals. The compositions of the present invention can be presented for administration to humans and animals in unit dosage forms, such as tablets, capsules, pills, powders, granules, sterile parenteral solutions or suspensions, oral solutions or suspensions, oil in water and water in oil emulsions containing suitable quantities of the compound, suppositories and in fluid suspensions or solutions.

For oral administration, either solid or fluid unit dosage forms can be prepared. For preparing solid compositions such as tablets, the compound can be mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other insert oil.

Fluid unit dosage forms for oral administration such as syrups, elixirs, and suspensions can be prepared. The forms can be dissolved in an aqueous vehicle together, with sugar, aromatic flavoring agents and preservatives to form a syrup. Suspensions can be prepared with an aqueous vehicle with the aid of a suspending agent such as acacia, tragacanth, methylcellulose and the like.

For parenteral administration, fluid unit dosage forms can be prepared utilizing the compound and a sterile vehicle. In preparing solutions the compound can be dissolved in water for injection and filter sterilized before filling into a suitable vial or ampoule and sealing. Adjuvants such as a local anesthetic, preservative and buffering agents can be dissolved in the vehicle. The composition can be frozen after filling into a vial and the water removed under vacuum. The composition can be frozen after filling into a vial and the water removed under vacuum. The dry lyophilized powder can then be sealed in the vial and reconstituted prior to use.

The following examples further demonstrate in greater detail the preparation of the bivalent ligands of the subject invention.

EXAMPLE 1

2,2'-(1,3-Propanediylbis(4,1-piperidinediylmethylidyne))bis(4,8-dimethoxybenzo (1,2-b: 5,4-b')difuran-3(2H)-one (Compound III, Table 1)

6-Bromofurochromone (6.50 g, 20.0 mmol), trimethylene-4,4-piperidine (2.1 g, 10 mmol) and potassium carbonate (5.52 g, 40.0 mmol) are added to acetonitrile (100 ml) and heated at 60° C. for 6 hours. The reaction is cooled to room temperature and diluted with water and vigorously stirred for 5–10 minutes. The solid that filled the flask is collected on a filter and air dried to yield 5.68 g (81.4%) the product as a brick red solid. An analytical sample is prepared by three recrystallizations form $CHCl_3/CH_3CN$ and drying the compound in a heating pistol. These recrystallizations remove the red color and small amounts of a more polar impurity to yield the biligand compound in relatively pure form.

Physical characteristics are as follows:
MP: 246° C.
Anal. Calc'd for $C_{39}H_{42}N_2O_{10}$: C, 67.04, H, 6.01; N, 4.01;
Found: C, 66.70; H, 6.13; N, 4.08.

EXAMPLE 2

7,7'-(1,2-Ethanediylbis(4,1-piperidinediylmethylene))-bis(4,9-dimethoxy-5H-furo (3,2-g)(1)-benzopyran-5-one (Compound Ia, Table 2)

The allylic iodide (50 g, 129 mmol) is added to a mixture of $CH_2CL_2$ (125 ml) and $CH_3OH$ (200 ml). To that solution is then added triethylamine (13.03 g, 129 mmol) followed by the bisamine (10.6 g, (92% pure), 49.7 mmol) in methanol (125 ml) dropwise and the resulting reaction stirred at room temperature overnight. The reaction is then diluted with methanol (2.5 l) and the resulting solid collected on a filter to give 26.2 g, 76% of analytically pure biligand compound.

Physical characteristics are as follows:
MP; 177°–79° C. (can be recrystallized from $CH_3CN$).
Anal. Calc'd for $C_{40}H_{44}N_2O_{210}$: C, 67.40; H, 6.22; N, 3.93.
Found: C, 67.21; H, 6.31; N, 3.84.

EXAMPLE 3

7,7'-(1,2-Ethanediylbis(4, 1-piperazinediylmethylene))bis (4.9-dimethoxy-5H-furo (3,2-g)(1)benzopyran-5-one (Compound Ib, Table 2)

A) Preparation of Diamine tether, 1,1'-(1,2-Ethanediyl)bispiperazine

N-Benzylpiperazine (25 g, 142 mmol), 1,2-dibromoethane (13.4 g, 71 mmol) and potassium carbonate are added to dimethylformamide (DMF) (100 ml) and stirred at room temperature for 3 days. The reaction is diluted with water and stirred for an additional 30 minutes. The white solid that filled the flask is collected on a filter to yield, after air drying, 20 g (79.6%) of the title product as a white fluffy solid.

This product (15.0 g, 42.3 mmol) is added to a parr hydrogenation bottle and dissolved in ethanol (EtOH) (50 ml). 10% palladium/carbon (Pd/C) (10.0 g) is added and the reaction is placed under a hydrogen atmosphere (45 psi) at room temperature with shaking for 24 hours. The catalyst is removed by filtration and the ethanol removed in vacuo to leave a viscous oil. That oil is dissolved in chloroform ($CHCl_3$), dried with magnesium sulfate ($MgSO_4$), and the solvent removed in vacuo to yield 6.6 g (78.8%) of the desired diamine tether.

B) Preparation of Biligand Compound

Allylic iodide (772 mg, 2.0 mmol) and the diamine tether (198 mg, 1.0 mmol) are added to acetonitrile (15 ml). To that mixture is added potassium carbonate (552 mg, 4.0 mmol) and the reaction heated at reflux for 2.5 hours. The reaction is cooled to room temperature and diluted with an equal volume of water. The solid that filled the flask is collected on a filter to yield 443 mg (62.2%) or pure product. An analytical sample is prepared by recrystallization from acetonitrile.

Physical characteristics are as follows:
MP: 184°–186° C.
Analytically Calculated for $C_{38}H_{42}N_4O_8$: C, 63.86; H, 5.88; N, 7.84;
Found: C, 63.48; H, 5.86; N, 7.78.

EXAMPLE 4

7,7'-((2-Hydroxy-1,3-propanediyl)bis(4,1-piperazinediylmethylene))bis(4,9-dimethoxy-5H-furo(3,2g)benzopyran-5-one (compound Ic, Table 2)

A) Preparation of 1-((Piperazinyl)methyl)-1-piperazineethanol tether

N-Benzylpiperazine (25 g, 142 mmol), epichlorohydrin (6,6 g, 71 mmol), sodium iodide (1.0 g) and potassium carbonate (15 g) are added to CMF (100 ml) and stirred at room temperature for 3 days. The reaction is diluted with water and stirred for an additional 30 minutes. The white solid that filled the flask is collected on a filter to afford, after air drying, 8.9 g (59.2%) of the title product as a white solid.

The amino alcohol product (14.0 g, 34.3 mmol) is added to absolute EtOH (200 ml). 10% Pd/C (10 g) is added and the reaction hydrogenated at 50 psi for 24 hours. The catalyst is removed by filtration and the filtrate evaporated in vacuo. The resulting cloudy oil is taken up in chloroform and dried ($MgSO_4$). Evaporation of the solvent affords 7.02 g (89.8%) of the title product as a clear oil. This material is used without further purification.

B) Preparation of Biligand Compound

The allylic iodide (5.21 g, 13.5 mmol) and diamine tether (1.54 g, 6.75 mmol) are added to acetonitrile (50 ml). To that mixture is added potassium carbonate (3.72 g, 27.0 mmol) and the reaction heated at reflux for three hours. The reaction is cooled to room temperature and diluted with an equal volume of water. The reaction is extracted with $CHCl_3$, dried and solvent removed in vacuo. The crude product (5 g) is chromatographed over 100 g of silica gel eluting first with $CHCl_3$, then 5–10% $CH_3OH/CHCl_3$. This affords 2.76 g (54.9%) of a light tan foam.

Physical characteristic are as follows:
Exact Mass calc'd for $C_{39}H_{44}N_4O_{11}$: 745.3085. Found: 745.3078.
Anal Calc'd for $C_{39}H_{44}N_4O_{11}$; C, 62.90; H, 5.91; N, 7.52
Found: C, 62.27; H, 6.08; NB, 7.24.

EXAMPLE 5

7,7'-(4,4'Bipiperidine)-1,1'-diylbis(4,9-dimethoxy-5H-furo(3,2-g)(1)benzopyran-5-one) (compound Id, Table 2)

A mixture of allylic iodide (3.86 g, 10 mmol) amine (670 mg, 4 mmol) and triethylamine (1.01 g, 10 mmol) is stirred at room temperature in $CH_3OH$ (10 ml) for 18 hours. The reaction is diluted with $CH_3OH$ (250 ml), filtered and washed with $CH_3OH$ and water. Recrystallization from $CH_3OH/CH_2Cl_2$ affords 1.64 g of the biligand compound.

Physical characteristics are as follows:
MP 126°-129° C.
Anal. Cal'd for $C_{38}H_{40}N_2O_{10}$: C, 66.66; H, 5.89; N, 4.09; Found: C, 65.96; H, 5.58; N, 4.02.

EXAMPLE 6

7,7'-(1,2-Ethanediylbis(4,1-piperidinediylmethylene))-bis-2,3-dihydro-4,9-dimethoxy-5H-furo(3.2-g)(1)benzopyran-5-one (Compound VI, Table 3)

NaH ({50% oil dispersion}, 13.1 g, 272 mmol) is added to a 1l three-neck round-bottom flask. The material is thoroughly washed with hexane and the hexane replaced with THF (300 ml). 2,3-Dihydro-khellinone (19.0 g, 79.8 mmol) is dissolved in ethyl thiomethylacetate (180 ml) and the solution is added dropwise over one hour to the NaH/THF slurry. There is a slight exotherm. The reaction is stirred at room temperature for two hours at which time TLC (5% $EtOAc/CH_2Cl_2$) indicates that the condensation reaction is complete. The solvent is removed in vacuo and the resulting oil is diluted with an equal volume of $CH_2Cl_2$ and poured into $CH_2Cl_2$, saturated with anhydrous HCl and stirred at room temperature for five hours. The reaction is evaporated in vacuo, washed with water and chromatographed over 800 g of silica gel. The column affords 8.2 g (33.4%) of the 4,9-dimethoxy-2,3-dihydro-((7-methylthio)methyl)-5H-furo(3,2-b)-benzopyran-5-one as a tan solid.

The tan product (6.0 g, 19.5 mmol) is dissolved in a mixture of $CH_2Cl_2/CH_3I$ (1/3; 20 ml) and heated at reflux for 65 hours. The reaction is evaporated in vacuo and triturated with $CH_2Cl_2$ (4x), discarding the solid each time (product is in the organic filtrate). The solvent is finally removed in vacuo to yield 6.25 g of 4,.9-dimethoxy-2,3-dihydro-((7-dihydro-((7-methtylthio)-methyl)-5H-furo (3,2-b)-benzopyran-5-one, which is used without further purification.

To a $CH_2Cl_2/CH_3OH$ mixture of the allylic iodide (2.5 g, 6.44 mmol) is added triethylaine (0.54 g, 5.38 mmol). The bisamine (0.53 g, 2.69 mmol (92% pure)) is then added in $CH_2OH$ dropwise over several minutes. After stirring at room temperature overnight, the reaction is filtered and the solid washed with $CH_3OH$ and dried to yield 0.93 g of pure product. Analytical sample is prepared from $CH_3OH/CH_2Cl_2$.

Physical characteristics are as follows:
MP: 204°-206° C.
Anal. Calc'd for $C_{40}H_{48}N_2O_{10}$: C, 67.02; H, 6.75; N, 3.91; Found; C, 66.73; H, 6.73; N, 3.88.

EXAMPLE 7

2,2'(1,4-Piperazinediylbis(3,1-propanediyliminomethylidyne))-bis (4,8dimethoxybenzo(1,2-b;5,4-b')difuran-3(2H)-one (compound VIII, Table 4)

6-Bromofurochromone (6.50 g, 20.0 mmol), 1,4-bis-(aminopropylpiperazine (2.0 g, 10 mmol) and potassium carbonate (5.52 g, 40.0 mmol) are added to acetonitril (100 ml) and heated at 60° C. for 5 hours. The reaction is cooled to room temperature and diluted with water and vigorously stirred for 5-10 minutes. The solid that filled the flask is collected on a filter and air dried to yield 6.37 g (92.6%) of the biligand as a tan solid. An analytical sample is prepared by recrystallization from DMF (6.37 g) gives 5.6 g (81.4%).

Physical characteristics are as follows:
MP: 239° C.
Anal. Calc'd for $C_{36}H_{40}N_4O_{10}$; C, 62.79; H, 5.81; N, 8.13; Found: C, 62.30; H, 6.03; N, 8.21. Corrected for 0.28% water: C, 62.61; H, 5.79; N, 8.10.

EXAMPLE 8

2,2'-(1,8-Octanediylbis(iminomethylidyne))bis(4,8-dimethoxybenzo(1,2-b;5,4-b')difuran-3(2H)-one (Compound IX, Table 4)

6-Bromofurochromone (6.50 g, 20.0 mmol), 1,8-diaminooctane (1.44 g, 10 mmol) and potassium carbonate (5.52 g, 40.0 mmol) are added to acetonitrile (100 ml) and heated at 60° C. for 5 hours. The reaction is cooled to room temperature and diluted with water and vigorously stirred for 5-10 minutes. The solid that filled the flask is collected on a filter and air dried to yield 5.65 g (89.4%) of the product as a brown solid. A relatively pure sample of the biligand compound is prepared by recrystallizations from $CH_3CN$ and drying the compound in a heating pistol.

Physical characteristics are as follows:
MP: 148°-50° C.
Anal. Calc'd for $C_{34}H_{36}N_2O_{10}$: C, 64.55; H, 5.69; N, 4.43. Found: 64.44; H, 5.86; N, 4.46.

EXAMPLE 9

7,7'-(1,2-Ethanediylbis(4,1-piperidinediylmethylene))-bis(4,9-dimethoxy-2-(trimethylsilyl)-5H-furo(3,2 g)(1)benzopyran-5-one 4,9-dimethoxy-7-methyl-2-(trimethylsilyl)-5H-furo(3,2-g)(1)benzopyran-5-one (5.0 g, 13.2 mmol) is dissolved in methylene chloride (20 ml) and then diluted with methyl iodide (75 g, 530 mmol). The mixture is refluxed for four days. After cooling to room temperature, the reaction is filtered and excess methyl iodide and methylene chloride removed in vacuo. This affords 4.7 g of 4,9-dimethoxy-2-trimethylsilyl-7-iodomethyl-5H-furo(3,2-b)-benzopyran-5-oneofsufficient purity for use in the next step.

The allylic iodide is dissolved in a mixture of $CH_2Cl_2$ and $CH_3OH$ (10/15 ml). To that solution is added the bisamine in $CH_3OH$ (5 ml) and the reaction is stirred at room temperature overnight. The reaction is evaporated in vacuo and the resulting solid is slurried with cold $CH_3OH$ and filtered to afford 1.70 g (75.5%) of the biligand compound. An analytical sample is prepared by recrystallization from $CH_3OH/CH_2Cl_2$.

Physical characteristics are as follows:
MP: 84°-7° C.

Anal. Calc'd for $C_{46}H_{60}N_2O_{10}Si_2$: C, 64.46; H, 7.06; N, 3.27. Found: C, 64.07; H, 698; N, 3.31.

TABLE 1

Trimethylene-4,4-dipiperidine Tether

| Compound | R | % ACAT Inhibition (μg/ml) | IC$_{50}$ |
|---|---|---|---|
| I | (structure with OCH$_3$ groups, furochromone ketone) | 5 68%<br>10 84%<br>15 91% | 4.2 μg/ml |
| II | (structure with OCH$_3$ groups, amide) | 5 60%<br>10 89%<br>15 97% | 1.8 μg/ml |
| III | (structure with OCH$_3$ groups, ketone) | 5 18%<br>10 29%<br>15 52% | |
| IV* | (structure with OCH$_3$ groups and CH$_3$-piperidine) | 5 10%<br>10 27%<br>15 39% | |

*Not a bivalent ligand of the subject invention

TABLE 2

Variation of the Amine Tether in the Furochromone System

| Compound | Amine Tether | % ACAT Inhibition (μg/ml) | IC$_{50}$ |
|---|---|---|---|
| I | (dipiperidine trimethylene tether) | 5 68%<br>10 84%<br>15 91% | 4.2 μg/ml |

TABLE 2-continued
Variation of the Amine Tether in the Furochromone System
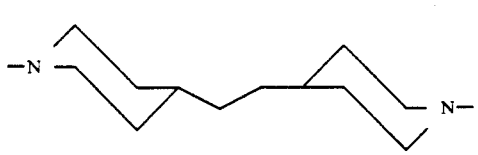
| Compound | Amine Tether | % ACAT Inhibition (μg/ml) | | IC$_{50}$ |
|---|---|---|---|---|
| Ia | 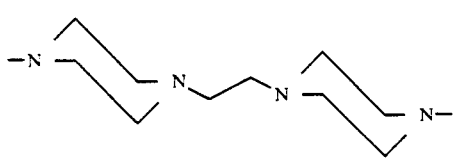 | 5 | 87% | 0.8 μg/ml |
|  |  | 10 | 84 |  |
|  |  | 15 | 75% |  |
| Ib | 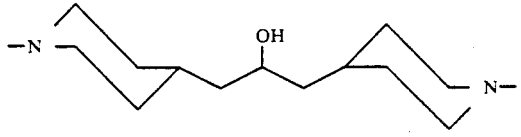 | 5 | 5% |  |
|  |  | 10 | 6% |  |
|  |  | 15 | 2% |  |
| Ic | 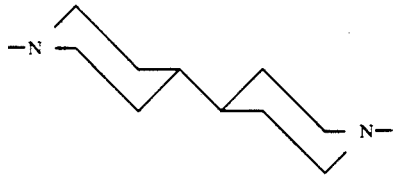 | 5 | 7% |  |
|  |  | 10 | 13% |  |
|  |  | 15 | 15% |  |
| Id | 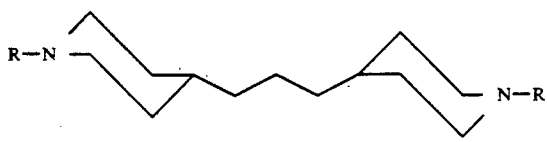 | 5 | 0% |  |
|  |  | 10 | 0% |  |
|  |  | 15 | 0% |  |
TABLE 3
Modifications of the Furochromone Nucleus with the 1,2-Ethanediyl-(4,4-dipiperidine) Tether
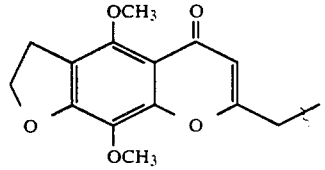
| Compound | R | % ACAT Inhibition (μg/ml) | | IC$_{50}$ |
|---|---|---|---|---|
| V | (structure shown) | 5 | 63% | 3.0 μg/ml |
|  |  | 10 | 73% |  |
|  |  | 15 | 74% |  |

TABLE 3-continued

Modifications of the Furochromone Nucleus with the
1,2-Ethanediyl-(4,4-dipiperidine) Tether

| Compound | R | % ACAT Inhibition (μg/ml) | | IC$_{50}$ |
|---|---|---|---|---|
| VI | 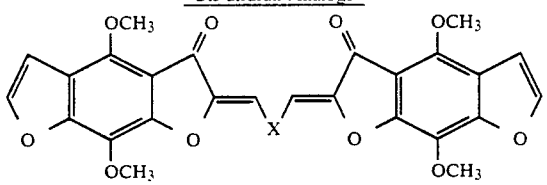 | 5 | 18% | |
| | | 10 | 29% | |
| | | 15 | 52% | |

TABLE 4

Bis-difuran Analogs

| Compound | X | % ACAT Inhibition (μg/ml) | | IC$_{50}$ |
|---|---|---|---|---|
| VII | | 5 | 18% | |
| | | 10 | 29% | |
| | | 15 | 52% | |
| VIII | | 5 | 32% | |
| | | 10 | 41% | |
| | | 15 | 49% | |
| IX | —HN(CH$_2$)$_n$NH— | 5 | 63% | |
| | | 10 | 52% | |
| | | 15 | 51% | |
| Difuran Analog* | | 5 | 47% | |
| | | 10 | 55% | |
| | | 15 | 65% | |
| Difuran Analog* | | 5 | 50% | |
| | | 10 | 66% | |
| | | 15 | 78% | |

*Not compounds of the subject invention.

HETEROCYCLIC COMPOUNDS "α"

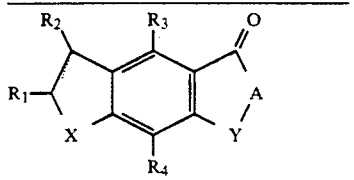

TETHERS "β"

TABLE 4-continued

A) 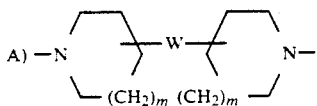

B) 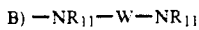

C) 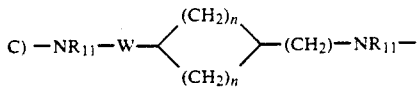

D) 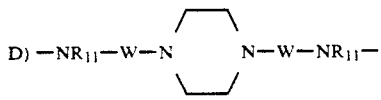

E) 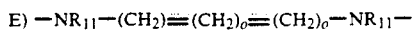

We claim:
1. A bivalent ligand α-β-α wherein α is structurally represented by the formula

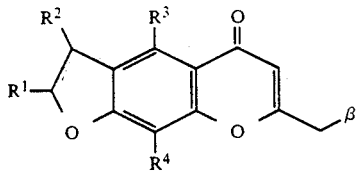

or a pharmaceutically acceptable salt thereof wherein:
$R^1$ and $R^2$ are independently:
 a) H,
 b) halo,
 c) $C_{1-8}$ alkyl,
 d) —$(CH_2)_p$-aryl,
 e) —$(CH_2)_p$-heteroaryl,
 f) —$(CH_2)_p$—$CO_2R^6$,
 g) —$(CH_2)_p$—$CONR^7R^8$,
 h) —$Si(R^9)$,
 i) —$(CH_2)_n$—$NR^7R^8$,
 j) —$(CH_2)_n$—$OR^{10}$,
 k) —$CF_3$, or
 l) —$(CH_2)_n$—$SR^6$, —$(CH_2)_n$—$SOR^6$, —$(CH_2)_n$—$SO_2R^6$;
$R^3$ is
 a) OH,
 b) $OCH_2CH=CH_2$,
 c) $OCH_2CH(OH)CH_2NHR^6$,
 d) —O—$C_{1-8}$ alkyl,
 e) —O—$(CH_2)_n$—$CO_2R^6$, or
 f) —O—$(CH_2)_n$—$CONR^7R^8$;
$R^4$ is
 a) hydrogen,
 b) halo,
 c) $NO_2$,
 d) $NH_2$
 e) $CF_3$,
 f) $C_{1-8}$ alkyl,
 g) aryl,
 h) —S—$C_{1-8}$ alkyl or aryl,
 i) —SO—$C_{1-8}$ alkyl or aryl,
 j) —$SO_2$—$C_{1-8}$ alkyl or aryl,
 k) $R^3$, or
 l) —$CH_2)_n$—$NR^7R^8$;

$R^6$ is H, $CF_3$, alkyl or aryl, $Li^+$, $Na^+$, $K^+$, $Ca^{2+}$ and other pharmaceutically acceptable counter ions for carboxylic acids;
$R^7$ and $R^8$ and H, CO-alkyl, CO-aryl, alkyl, cycloalkyl, alkylaryl, aryl, heteroalkyl, aryl, or $R^7$ and $R^8$ can be taken together to form a piperidine ring or morpholine ring;
$R^9$ is an $C_{1-8}$ alkyl or aryl;
$R^{10}$ is H, $CF_3$, $C_{1-8}$ alkyl, aryl or heteroaryl; and
n is 0–5 and p is 0–8; and
β is

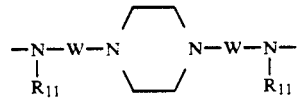

wherein:
W is —$(CH_2)_n$— where n is 0–5 and
$R^{11}$ is H, $C_{1-8}$ alkyl, CO—$C_{1-8}$ alkyl or CON—$C_{1-8}$ alkyl or -aryl;
where aryl is an aromatic mono or bicyclic, optionally substituted, $C_6$-$C_{12}$ group;
where heteroaryl is a mono or bicyclic hetero aryl having one N, O, S or two N atoms substituted for one or two carbon atoms;
where heteroalkyl is a 2 to 8 carbon atom alkyl having one N, O, S or two N atoms substituted for one or two carbon atoms.
2. The compound of claim 1 wherein said -β- from the bivalent ligand α-β-α is:
 a) 1,4-bis(aminopropylpiperazine).
3. A method for preventing or treating atherosclerosis comprising: administering to a patient in need thereof a therapeutically effective amount of bivalent ligand α-β-α wherein α is structurally represented by the formula

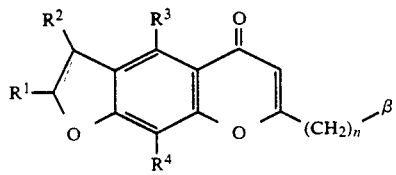

or a pharmaceutically acceptable salt thereof wherein:

$R^1$ and $R^2$ are independently:
  a) H,
  b) halo,
  c) $C_{1-8}$ alkyl,
  d) $-(CH_2)_p$-aryl,
  e) $-(CH_2)_p$-heteroaryl,
  f) $-(CH_2)_p-CO_2R^6$,
  g) $-(CH_2)_p-CONR^7R^8$,
  h) $-Si(R^9)$,
  i) $-(CH_2)_n-NR^7R^8$,
  j) $-(CH_2)_n-OR^{10}$,
  k) $-CF_3$, or
  l) $-(CH_2)_n-SR^6$, $-(CH_2)_n-SOR^6$, $-(CH_2)_n-SO_2R^6$;

$R^3$ is
  a) OH,
  b) $OCH_2CH=CH_2$,
  c) $OCH_2CH(OH)CH_2NHR^6$,
  d) $-O-C_{1-8}$ alkyl,
  e) $-O-(CH_2)_n-CO_2R^6$, or
  f) $-O-(CH_2)_n-CONR^7R^8$;

$R^4$ is
  a) hydrogen,
  b) halo,
  c) $NO_2$,
  d) $NH_2$
  e) $CF_3$,
  f) $C_{1-8}$ alkyl,
  g) aryl,
  h) $-S-C_{1-8}$ alkyl or aryl,
  i) $-SO-C_{1-8}$ alkyl or aryl,
  j) $-SO_2-C_{1-8}$ alkyl or aryl,
  k) $R^3$, or
  l) $-(CH_2)_n-NR^7R^8$;

$R^6$ is H, $CF_3$, alkyl or aryl, $Li^+$, $Na^+$, $K^+$, $Ca^{2+}$ and other pharmaceutically acceptable counter ions for carboxylic acids;

$R^7$ and $R^8$ are H, CO-alkyl, CO-aryl, alkyl, cycloalkyl, alkylaryl, aryl, heteroalkyl, aryl, or $R^7$ and $R^8$ can be taken together to form a piperidine ring or morpholine ring;

$R^9$ is an $C_{1-8}$ alkyl or aryl;

$R^{10}$ is H, $CF_3$, $C_{1-8}$ alkyl, aryl or heteroaryl;

n is 0-5 and p is 0-8; and $\beta$ is

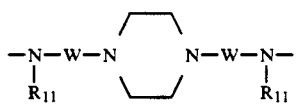

wherein:

W is $-(CH_2)_n-$ where n is 0-5 and $R^{11}$ H, $C_{1-8}$ alkyl, $CO-C_{1-8}$ alkyl or $CON-C_{1-8}$ alkyl or -aryl;

where aryl is an aromatic mono or bicyclic, optionally substituted, $C_6-C_{12}$ group;

where heteroaryl is a mono or bicyclic hetero aryl having one N, O, S or two N atoms substituted for one or two carbon atoms;

where heteroalkyl is a 2 to 8 carbon atom alkyl having one N, O, S or two N atoms substituted for one or two carbon atoms.

4. The method of claim 3 wherein said bivalent ligand is administered by oral, transdermal or parenteral means.

5. The method of claim 4 wherein said bivalent ligand is administered in an amount of from about 0.1 to about 1000 mg/kg per dose.

6. A method for blocking or inhibiting ACAT enzyme comprising:
  administering to a patient a therapeutically effective amount of a bivalent ligand $\alpha$-$\beta$-$\alpha$ wherein $\alpha$ is structurally represented by the formula

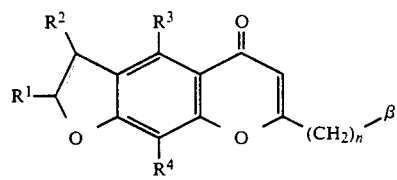

or a pharmaceutically acceptable salt thereof wherein:

$R^1$ and $R^2$ are independently:
  a) H,
  b) halo,
  c) $C_{1-8}$ alkyl,
  d) $-(CH_2)_p$-aryl,
  e) $-(CH_2)_p$-heteroaryl,
  f) $-(CH_2)_p-CO_2R^6$,
  g) $-(CH_2)_p-CONR^7R^8$,
  h) $-Si(R^9)$,
  i) $-(CH_2)_n-NR^7R^8$,
  j) $-(CH_2)_n-OR^{10}$,
  k) $-CF_3$, or
  l) $-(CH_2)_n-SR^6$, $-(CH_2)_n-SOR^6$, $-(CH_2)_n-SO_2R^6$;

$R^3$ is
  a) OH,
  b) $OCH_2CH=CH_2$,
  c) $OCH_2CH(OH)CH_2NHR^6$,
  d) $-O-C_{1-8}$ alkyl,
  e) $-O-(CH_2)_n-CO_2R^6$, or
  f) $-O-(CH_2)_n-CONR^7R^8$;

$R^4$ is
  a) hydrogen,
  b) halo,
  c) $NO_2$,
  d) $NH_2$
  e) $CF_3$,
  f) $C_{1-8}$ alkyl,
  g) aryl,
  h) $-S-C_{1-8}$ alkyl or aryl,
  i) $-SO-C_{1-8}$ alkyl or aryl,
  j) $-SO_2-C_{1-8}$ alkyl or aryl,
  k) $R^3$, or
  l) $-(CH_2)_n-NR^7R^8$;

$R^6$ is H, $CF_3$, alkyl or aryl, $Li^+$, $Na^+$, $K^+$, $Ca^{2+}$ and other pharmaceutically acceptable counter ions for carboxylic acids;

$R^7$ and $R^8$ are H, CO-alkyl, CO-aryl, alkyl, cycloalkyl, alkylaryl, aryl, heteroalkyl, aryl, or $R^7$ and $R^8$ can be taken together to form a piperidine ring or morpholine ring;

$R^9$ is an $C_{1-8}$ alkyl or aryl;

$R^{10}$ is H, $CF_3$, $C_{1-8}$ alkyl, aryl or heteroaryl;

n is 0-5 and p is 0-8; and $\beta$ is

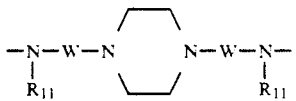

wherein:

W is —(CH$_2$)$_n$— where n is 0-5 and

R$^{11}$ is H, C$_{1-8}$ alkyl, CO—C$_{1-8}$ alkyl or CON—C$_{1-8}$ alkyl or —aryl;

where aryl is an aromatic mono or bicyclic, optionally substituted, C$_6$-C$_{12}$ group;

where heteroaryl is a mono or bicyclic hetero aryl having one N, O, S or two N atoms substituted for one or two carbon atoms;

where heteroalkyl is a 2 to 8 carbon atom alkyl having one N, O, S or two N atoms substituted for one or two carbon atoms.

7. The method of claim 6 wherein said bivalent ligand is administered by oral, transdermal or parenteral means.

8. The method of claim 6 wherein said bivalent ligand is administered in an amount of from about 0.1 to about 1000 mg/kg per dose.

9. The method of claim 6 wherein said bivalent ligand is administered subsequent to a, coronary by-pass surgery, angioplasty or heart transplant.

10. The method of claim 6 wherein said bivalent ligand is used for the treatment of hypertriglyceridemia, chylomicronemia, eruptive xanthomata, hepatomegaly, abdominal pain, pancreatitis, dyspnea, or related disorders of the triglyceride metabolic system.

11. A method for lowering plasma triglycerides comprising:

administering to a patient in need thereof a therapeutically effective amount of a bivalent ligand $\alpha$-$\beta$-$\alpha$ wherein $\alpha$ is structurally represented by the formula

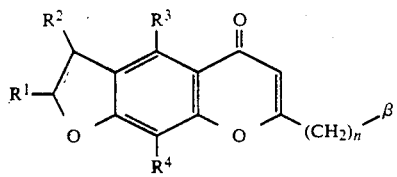

or a pharmaceutically acceptable salt thereof wherein:

R$^1$ and R$^2$ are independently:
a) H,
b) halo,
c) C$_{1-8}$ alkyl,
d) —(CH$_2$)$_p$-aryl,
e) —(CH$_2$)$_p$-heteroaryl,
f) —(CH$_2$)$_p$—CO$_2$R$^6$,
g) —(CH$_2$)$_p$—CONR$^7$R$^8$,
h) —Si(R$^9$),
i) —(CH$_2$)$_n$—NR$^7$R$^8$,
j) —(CH$_2$)$_n$—OR$^{10}$,
k) —CF$_3$, or
l) —(CH$_2$)$_n$—SR$^6$, —(CH$_2$)$_n$—SOR$^6$, —(CH$_2$)$_n$—SO$_2$R$^6$;

R$^3$ is
a) OH,
b) OCH$_2$CH=CH$_2$,
c) OCH$_2$CH(OH)CH$_2$NHR$^6$,
d) —O—C$_{1-8}$ alkyl,
e) —O—(CH$_2$)$_n$—CO$_2$R$^6$, or
f) —O—(CH$_2$)$_n$—CONR$^7$R$^8$;

R$^4$ is
a) hydrogen,
b) halo,
c) NO$_2$,
d) NH$_2$
e) CF$_3$,
f) C$_{1-8}$ alkyl,
g) aryl,
h) —S—C$_{1-8}$ alkyl or aryl,
i) —SO—C$_{1-8}$ alkyl or aryl,
j) —SO$_2$—C$_{1-8}$ alkyl or aryl,
k) R$^3$, or
l) —(CH$_2$)$_n$—NR$^7$R$^8$;

R$^6$ is H, CF$_3$, alkyl or aryl, Li$^+$, Na$^+$, K$^+$, Ca$^{2+}$ and other pharmaceutically acceptable counter ions for carboxylic acids;

R$^7$ and R$^8$ are H, CO-alkyl, CO-aryl, alkyl, cycloalkyl, alkylaryl, aryl, heteroalkyl, aryl, or R$^7$ and R$^8$ can be taken together to form a piperidine ring or morpholine ring;

R$^9$ is an C$_{1-8}$ alkyl or aryl;

R$^{10}$ is H, CF$_3$, C$_{1-8}$ alkyl, aryl or heteroaryl;

n is 0-5 and p is 0-8; and $\beta$ is

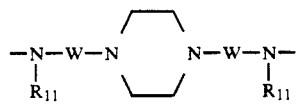

wherein:

W is —(CH$_2$)$_n$— where n is 0-5 and

R$^{11}$ is H, C$_{1-8}$ alkyl, CO—C$_{1-8}$ alkyl or CON—C$_{1-8}$ alkyl or —aryl;

where aryl is an aromatic mono or bicyclic, optionally substituted, C$_6$-C$_{12}$ group;

where heteroaryl is a mono or bicyclic hetero aryl having one N, O, S or two N atoms substituted for one or two carbon atoms;

where heteroalkyl is a 2 to 8 carbon atom alkyl having one N, O, S or two N atoms substituted for one or two carbon atoms.

12. The method of claim 11 wherein said bivalent ligand is administered by oral, transdermal or parenteral means.

13. The method of claim 11 wherein said bivalent ligand is administered in an amount of from about 0.1 to about 1000 mg/kg per dose.

14. A method for elevating HDL cholesterol comprising:

administering to a patient a therapeutically effective amount of a bivalent ligand $\alpha$-$\beta$-$\alpha$ wherein $\alpha$ is structurally represented by the formula

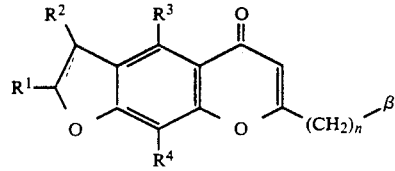

or a pharmaceutically acceptable salt thereof wherein:

$R^1$ and $R^2$ are independently:
a) H,
b) halo,
c) $C_{1-8}$ alkyl,
d) —$(CH_2)_p$—aryl,
e) —$(CH_2)_p$—heteroaryl,
f) —$(CH_2)_p$—$CO_2R^6$,
g) —$(CH_2)_p$—$CONR^7R^8$,
h) —$Si(R^9)$,
i) —$(CH_2)_n$—$NR^7R^8$,
j) —$(CH_2)_n$—$OR^{10}$,
k) —$CF_3$, or
l) —$(CH_2)_n$—$SR^6$, —$(CH_2)_n$—$SOR^6$, —$(CH_2)_n$—$SO_2R^6$;

$R^3$ is
a) OH,
b) $OCH_2CH=CH_2$,
c) $OCH_2CH(OH)CH_2NHR^6$,
d) —O—$C_{1-8}$ alkyl,
e) —O—$(CH_2)_n$—$CO_2R^6$, or
f) —O—$(CH_2)_n$—$CONR^7R^8$;

$R^4$ is
a) hydrogen,
b) halo,
c) $NO_2$,
d) $NH_2$,
e) $CF_3$,
f) $C_{1-8}$ alkyl,
g) aryl,
h) —S—$C_{1-8}$ alkyl or aryl,
i) —SO—$C_{1-8}$ alkyl or aryl,
j) —$SO_2$—$C_{1-8}$ alkyl or aryl,
k) $R^3$, or
l) —$(CH_2)_n$—$NR^7R^8$;

$R^6$ is H, $CF_3$, alkyl or aryl, $Li^+$, $Na^+$, $Ca^{2+}$ and other pharmaceutically acceptable counter ions for carboxylic acids;

$R^7$ and $R^8$ are H, CO-alkyl, CO-aryl, alkyl, cycloalkyl, alkylaryl, aryl, heteroalkyl, aryl, or $R^7$ and $R^8$ can be taken together to form a piperidine ring or morpholine ring;

$R^9$ is an $C_{1-8}$ alkyl or aryl;

$R^{10}$ is H, $CF_3$, $C_{1-8}$ alkyl, aryl or heteroaryl;

n is 0-5 and p is 0-8; and

β is

wherein:
W is —$(CH_2)_n$— where n is 0-5 and
$R^{11}$ is H, $C_{1-8}$ alkyl, CO-$C_{1-8}$ alkyl or CON-$C_{1-8}$ alkyl or —aryl;

where aryl is an aromatic mono or bicyclic, optionally substituted, $C_6$-$C_{12}$ group;

where heteroaryl is a mono or bicyclic hetero aryl having one N, O, S or two N atoms substituted for one or two carbon atoms;

where heteroalkyl is a 2 to 8 carbon atom alkyl having one N, O, S or two N atoms substituted for one or two carbon atoms.

15. The method of claim 14 wherein said bivalent ligand is administered by oral, transdermal or parenteral means.

16. The method of claim 15 wherein said bivalent ligand is administered in an amount of from about 0.1 to about 1000 mg/kg per dose.

* * * * *